United States Patent [19]

Buffet

[11] Patent Number: 4,471,783
[45] Date of Patent: Sep. 18, 1984

[54] METHOD OF MAKING A CARDIAC STIMULATOR WITH A SINGLE ENCLOSURE FOR SEPARATING THE ELECTRIC CURRENT AND PULSE GENERATING MEANS

[75] Inventor: Jacques Buffet, Le Raincy, France

[73] Assignee: Cardiofrance-Compagnie Francaise d'Electrocardiologie, France

[21] Appl. No.: 361,804

[22] Filed: Mar. 25, 1982

[30] Foreign Application Priority Data

Mar. 27, 1981 [FR] France ............................. 81 06197

[51] Int. Cl.³ ............................................. A61N 1/00
[52] U.S. Cl. ............................................. 128/419 PS
[58] Field of Search ....... 128/419 P, 419 PG, 419 PS, 128/419 B; 429/191, 213; 29/623.1, 623.2

[56] References Cited

U.S. PATENT DOCUMENTS

| | | | |
|---|---|---|---|
| 3,649,367 | 1/1979 | Purdy | 128/419 PS |
| 3,735,766 | 5/1973 | Bowers et al. | 128/419 P |
| 4,135,519 | 1/1979 | Greatbatch | 128/419 PS |
| 4,164,070 | 8/1979 | Greatbatch et al. | 26/623.2 |
| 4,203,201 | 5/1980 | Mead et al. | 26/623.2 |
| 4,385,439 | 5/1983 | Mead et al. | 29/623.2 |

FOREIGN PATENT DOCUMENTS 1274882  5/1972  United Kingdom ............ 128/419 P

Primary Examiner—William E. Kamm
Assistant Examiner—Mitchell J. Shein
Attorney, Agent, or Firm—Darby & Darby

[57] ABSTRACT

This cardiac stimulator comprises a sealed metal case (2), means for generating electric direct current which are electrically connected to at least one electronic circuit (13) adapted to deliver heart-stimulating pulses, the current generating means, comprising an anode (3), a cathode (4) and an electrolyte, being disposed directly in the case (2). The electronic circuit (13) is enclosed in a sealed cell (12) provided with an output terminal (14) for electrically connecting an electrode (14') and another terminal (15) for electrically connecting one of the anode and cathode poles (3, 4). This stimulator has a low weight and reduced over-all dimensions.

2 Claims, 6 Drawing Figures

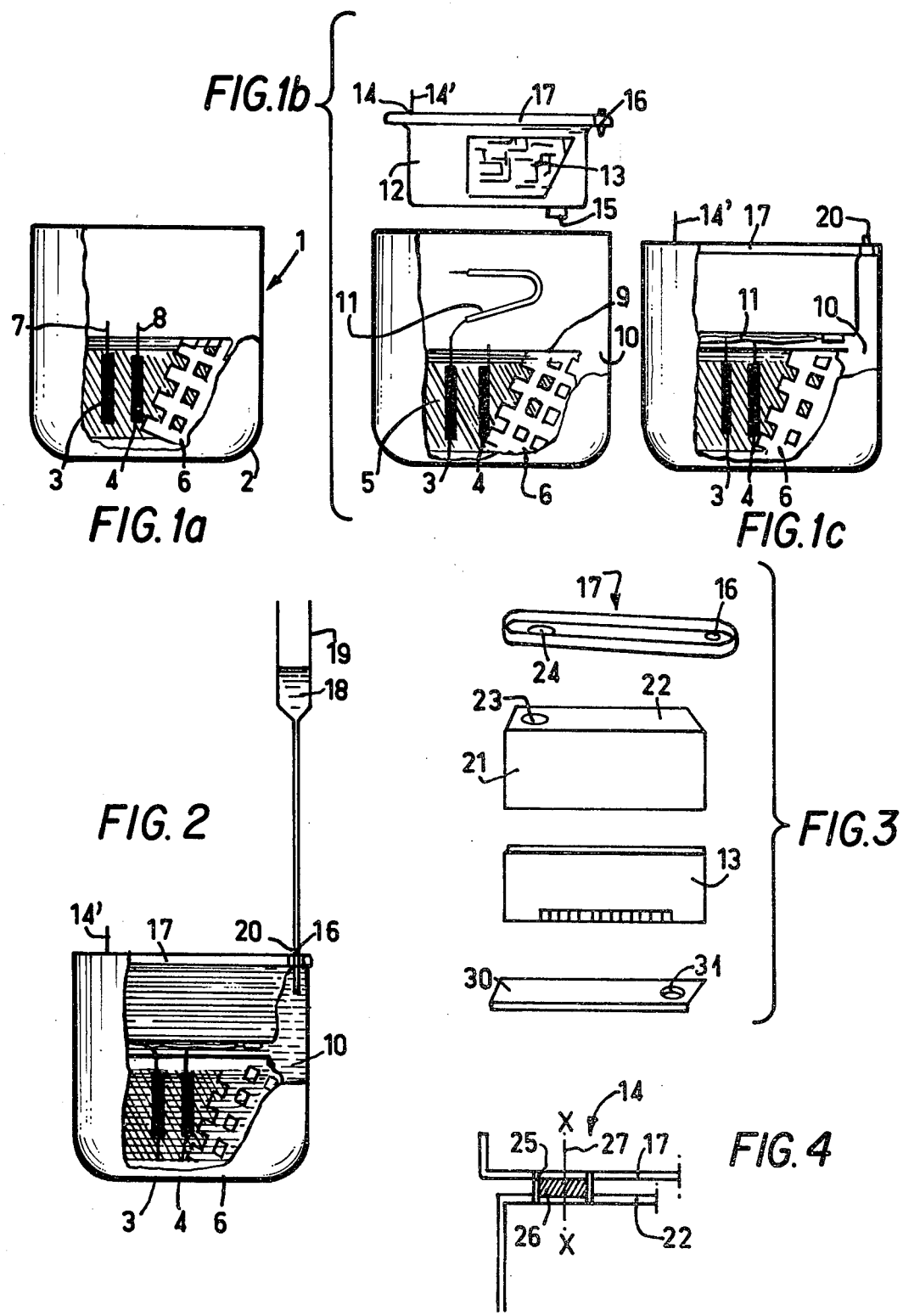

METHOD OF MAKING A CARDIAC STIMULATOR WITH A SINGLE ENCLOSURE FOR SEPARATING THE ELECTRIC CURRENT AND PULSE GENERATING MEANS

BACKGROUND OF THE INVENTION

1. Field of the Invention

This invention relates to cardiac stimulators and has specific reference to an improved apparatus of this character which has a reduced weight and reduced overall dimensions.

2. The Prior Art

Cardiac stimulators comprising a fluid-tight metal case capable of isolating the internal component sections from liquids such as blood or lymph circulating in the body cavity in which the stimulator is grafted are already known. In apparatus of this type a battery that does not release any gas is fitted in the case and consist of a dry battery cell enclosing an anode, a cathode and an electrolyte, one pole of the battery being connected to the metal case of the stimulator so as to earth same. Fitted in the stimulator case is another fluid-tight cell or sub-case containing electronic circuit means capable of generating transmitted either to the patient's heart or to a measuring apparatus serving inter alia the purpose of checking the proper operation of the stimulator. As a rule, the battery is a dry battery having a lithium anode and the electrolyte consisting of a liquid or solid material. The positive terminal of the battery is earthed by connecting same to the metal case. The negative terminal of the battery is connected to the electronic circuit having its earth electrically connected to the stimulator case. This stimulator case consists of titanium, a metal compatible with the liquids contained in the human body. Thus, hitherto known stimulators comprise a sealed chamber enclosing the electronic circuitry and separated from an equally sealed battery cell.

Stimulators according to this known technique are satisfactory in actual service; however, they are relatively heavy on account of their many metal walls and partitions. Now the trend is toward a miniaturization in devices of this kind in order to reduce the patient's discomfort likely to derive therefrom, and also to permit the grafting of devices of this type to very young children.

SUMMARY OF THE INVENTION

It is the primary object of the present invention to provide a cardiac stimulator of relatively reduced dimensions and weight, in comparison with stimulators of the prior art. Another object of the invention is to reduce the cost of cardiac stimulators.

These objects are achieved according to this invention by providing a cardiac stimulator of the kind broadly described hereinabove, of which the direct-current generators, i.e. an anode, a cathode and an electrolyte, are enclosed directly in the case. Thus, no fluid-tight enclosure is required for isolating these elements from the case proper or from the cell containing the electronic circuit means. The battery-forming elements and the electronic circuit means enclosed in a fluid-tight cell are introduced into the case and the cell proper is provided on the one hand with an output terminal connected for example to a pulse-electrode and on the other hand with another terminal connected to one of the battery poles. With this arrangement, a metal wall or partition is dispensed with, thus reducing appreciably the weight of the cardiac stimulator.

In order to afford a clearer understanding of the present invention and of the manner in which the same may be carried out in actual practice, reference will now be made to the accompanying drawing illustrating diagrammatically by way of example a typical form of embodiment of the invention.

THE DRAWING

FIGS. 1a, 1b and 1c are diagrammatic views showing the successive steps of the procedure contemplated for manufacturing a cardiac stimulator according to the teachings of this invention;

FIG. 2 is a diagram showing additional steps of the procedure for manufacturing a second form of embodiment of the stimulator of this invention;

FIG. 3 is a diagram showing an exploded view of the component elements of the means for assembling the case cover and the electronic circuit cell.

FIG. 4 is a diagram showing the construction of the output terminal.

DESCRIPTION OF THE PREFERRED EMBODIMENT

The cardiac stimulator 1 illustrated comprises a case 2 of substantially flat parallelipipedic configuration. This case is about fourcentimeter wide, and its length and thickness are about one centimeter. The case 2 consists of a suitable conducting material, for example a metal compatible with the body fluids, such as titanium. Direct-current generating means are introduced into this case. According to a first form of embodiment of the invention, said d.c. generators comprise an anode 3, a cathode 4, a solid electrolyte 5 and possibly a separator 6 or else, all these means being well known to those conversant with the art and therefore shown only diagrammatically in the drawing. The aforesaid elements are introduced in any suitable way, for example by force-fitting, into the case 2, so that they are wedged inthe case bottom. Output terminals 7 and 8 are disposed on the anode and cahtode 3 and 4, respectively. If desired, a circuit gasket 9 may be disposed on top of the current generating means. This gasket 9 may be fluid-tight, but in this specific form of embodiment it may be dispensed with. Thus, for instance, a gap 10 may be provided between the wall of case 2 and the gasket 9. This gasket consists preferably of plastic or silicone. The anode may consist for instance for lithium and the cathode of manganese dioxide, the elctrolyte being a solid substance. In this case the stimulator is transferred to an enclosure containing a relatively dry atomosphere, i.e. having a very low moisture content, or in vacuo, to prevent the water vapor from damaging the surface of the current generators, and more particularly lithium if the anode is made from this specific metal. The anode or cathode output terminal is connected to a conducting wire 11 and the other output terminal is connected to the ground-forming case 2.

Then a fluid-tight cell 12 containing one or more electronic circuits 13 is introduced into the case 2 above the gasket 9, said circuits being adapted to emit pulses for either stimulating the patient's heart or permitting of checking the proper opertion of the stimulator. This cell 12 consists of metal and comprises an output terminal 14 for connecting an electrode 14' delivering the pulses thus generated. The cell 12 further comprises a terminal 15 for connecting the wire 11 and therefore one of the anode or cathode poles. The output terminal 14 is disposed on one face of said cell, and terminal 15 is disposed on the opposite face. On the other hand, a hole 16 may be formed through the face comprising the output terminal 14. Besides, this cell 12 is positively connected to the case over (see FIG. 1b).

Then terminal 15 is connected to conducting wire 11. This terminal 15 is electrically connected to an outlet (not shown) of the electronic circuit or circuits having another outlet connected to the ground forming case. The fluid-tight cell 12 is subsequently introduced into the case 2, with the hole 16 registering with the gap 10. Finally, the case cover is sealed edge to edge to its cover 17, for example by welding. Under these conditions, the other pole of the current generating means is connected to the electronic circuit through this weld. Then the hole 16 is obturated.

It will be seen that in the first form of embodiment utilizing a solid electrolyte the gap 10 and hole 16 are useless and therefore can be dispensed with, so that no welding step is necessary for sealing the hole 16.

On the other hand, in a second form of embodiment of the invention the provision of said gap 10 and hole 16 is compulsory. In fact, the manufacturing steps are identical with those required for the first form of embodiment, except that the elctrolyte 5 is not introduced into the case before fitting the circuit cell 12. Therefore, the sequence of assembling steps take place as follows: the anode 3 and cathode 4 are firstly inserted into the case together with the separator 6. The output terminals 7, 8 and a gasket 9 comprising compulsorily (in this specific form of embodiment) a gap 10 are then introduced. Subsequently, the wire 11, terminal 15 and one of terminals 7, 8 are interconnected, the case 2 being grounded. The cell 12 is introduced into the case 2 and the cover 17 rigid with cell 12 is welded to the case 2. The cover 17 comprises necessarily a hole 16 which in the assembled condition registers with gap 10. This hole 16 is disposed in a lateral area of cover 17, preferably opposite the output terminal 14 of electrode 14'. The additional manufacturing step consists in filling the free space left between the case 2 and the fluid-tight cell 12 with a suitable liquid electrolyte 18 with the assistance of a plunging-siphon 19 (see FIG. 2). Then, hole 16 is sealed as in the preceding example. With the modified form of embodiment, the electrolyte fills up the complete free space, in contrast to hitherto known stimulators constantly exposed to the risk of leakage of the electrolyte into the free spaces or corners. The filling operation may be further facilitated by providing a small tube 20 extending through the hole 16. This tube 20 is eventually welded at the end of the manufacturing operation.

As already mentioned in the foregoing, the cover 17 of case 2 eventually forms an integral part of the cell 12 enclosing the electronic circuit or circuits 13 when this cell 12 is introduced into the case 2 (see FIG. 1b). Referring now to FIGS. 3 and 4 of the drawing, it will be seen that the following procedure is required for connecting the cover 17 of the stimulator to the fluid-tight cell 12: firstly, the cover 17 is disposed on one of the faces of an open box 21 preferably of parallelipipedic configuration. The face 22 of box 21 which has greatest surface area has a hole 23 formed there therethrough near one end thereof. The stimulator cover 17 has a hole 24 corresponding to this hole 23 formed through one of its endmost lateral portions and in the opposite lateral portion the cover 17 comprises a hole 16 through which the liquid electrolyte can subsequently be introduced into the assembly. The cover 17 is fitted on said face 22 of box 21. Then a cylindrical tubular member 25 having an axis of revolution XX is fitted into the aligned holes 23, 24, and a circular disc 26 is soldered to the inner wall of this tubular member 25; the circular disc 26 has a central axial hole formed therethrough and engaged by a conducting wire 27 constituting the teminal 14'. This disc 26 is made from a suitable insulating material such as ceramic in the form of sintered alumina. Then the cylindrical tubular member 25 is welded to the box and also to the cover 17. Thus, the outlet terminal 14 is obtained for connecting the pulse-emitter electrode 14'. Subsequently, the electronic circuit or circuits 13 is or are introduced into the open box and connected to terminal 14 and also to another teminal 15 located in said hole 31 formed through a bottom element 30 of the fluid-tight cell 12 thus obtained. Terminal 14 is the output terminal leading to the electrode, and terminal 15 is the output terminal leading to one of the battery poles.

Of course, though two specific forms of embodiment of the present invention have been described and illustrated herein, it will readily occur to those conversant with the art that various modifications and changes may be brought thereto without departing from the basic principle of the invention as set forth in the appended claims.

What is claimed as new is:

1. A method of manufacturing a cardiac stimulator having electronic circuitry enclosed by a sealed metal box, a first power supply input terminal electrically coupled to said metal box and a second power supply input terminal accessible from the outside of an insulated from said box, electrical power generating means comprising anode and cathode elements and a liquid electrolyte, a metal case adapted to contain generating means and said metal case having an open end, and a cover adapted for sealing said open end of said case, said method of manufacturing said stimulator comprising the steps of:

inserting anode and cathode elements into said metal case;

electrically coupling one of said anode and cathode elements to said metal case;

electrically coupling the other of said anode and cathode elements to said second power input termnal, providing a hole in said cover;

securing said metal box to the inner side of said cover and then inserting said metal box into said metal case in electrical contact therewith;

closing said metal case by welding said cover to the open end thereof;

introducing said liquid electrolyte into said case through said hole in said cover; and sealing said hole.

2. The method of claim 1 wherein the step of connecting said stimulator case cover to said sealed metal box containing said electronic circuitry comprises the steps of:

fitting the cover of said stimulator case, which has a hole formed therethrough, to one of the major faces of an open metal box preferably of substantially parallelipipedic configuration, said face having a hole formed therethrough in alignment with the hole of said cover hole, introducing a metal tubular member filled with a disc of insulating material into the holes of said case cover and said box, welding said metal tubular member to said box and said cover of the stimulator case in order to provide a sealed outlet terminal for connecting same to a pulse-emitting electrode, introducing the electronic circuitry into said open box, sealing said box by means of a cover comprising an output terminal for connecting same to one of said anode and cathode elements.

* * * * *